US012653476B2

(12) United States Patent
Roser et al.

(10) Patent No.: US 12,653,476 B2
(45) Date of Patent: Jun. 16, 2026

(54) COMPUTER-IMPLEMENTED METHOD AND DATA PROCESSING FACILITY FOR SCATTERED RADIATION CORRECTION AND FOR PARAMETERIZATION OF A DETERMINATION ALGORITHM FOR DETERMINING A MEASURE OF QUALITY, COMPUTER PROGRAM AND DATA MEDIUM

(71) Applicant: Siemens Healthineers AG, Forchheim (DE)

(72) Inventors: Philipp Roser, Erlangen (DE); Alexander Preuhs, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 153 days.

(21) Appl. No.: 18/782,407

(22) Filed: Jul. 24, 2024

(65) Prior Publication Data

US 2025/0032074 A1 Jan. 30, 2025

(30) Foreign Application Priority Data

Jul. 26, 2023 (DE) .................... 10 2023 207 125.8

(51) Int. Cl.
*G06N 20/00* (2019.01)
*A61B 6/00* (2024.01)
*A61B 6/03* (2006.01)

(52) U.S. Cl.
CPC .............. *A61B 6/483* (2013.01); *A61B 6/032* (2013.01); *A61B 6/5282* (2013.01); *G06N 20/00* (2019.01)

(58) Field of Classification Search
CPC ....... A61B 6/032; A61B 6/483; A61B 6/5282; G06N 20/00
See application file for complete search history.

(56) References Cited

U.S. PATENT DOCUMENTS

2021/0330274 A1* 10/2021 Birkhold .............. A61B 6/5282

OTHER PUBLICATIONS

Trapp, Philip, et al. "Empirical scatter correction: CBCT scatter artifact reduction without prior information." Medical Physics 49.7 (2022): 4566-4584.
Decision to Grant App. DE 10 2023 207 215.8 dated Apr. 9, 2024, with English translation.

* cited by examiner

*Primary Examiner* — Mark R Gaworecki
(74) *Attorney, Agent, or Firm* — Lempia Summerfield Katz LLC

(57) ABSTRACT
A computer-implemented method for scattered radiation correction, comprising the steps: obtaining projection images, optimizing a measure of quality by variation of correction parameters depending on the projection images, wherein a determination algorithm, which serves to determine the measure of quality, is an algorithm trained by machine learning and processes as its input data a reconstructed three-dimensional image dataset or processing data that is chosen from the image dataset, wherein the image dataset is based on corrected projection images, wherein a respective corrected projection image results from application of a correction algorithm, wherein the correction algorithm is parameterized by the correction parameters, provision of radiation scatter-corrected projection images and/or of a radiation scatter-corrected reconstructed three-dimensional image dataset.

13 Claims, 5 Drawing Sheets

FIG 3

COMPUTER-IMPLEMENTED METHOD AND DATA PROCESSING FACILITY FOR SCATTERED RADIATION CORRECTION AND FOR PARAMETERIZATION OF A DETERMINATION ALGORITHM FOR DETERMINING A MEASURE OF QUALITY, COMPUTER PROGRAM AND DATA MEDIUM

CROSS REFERENCE TO RELATED APPLICATIONS

This application claims the benefit DE 10 2023 207 125.8 filed on Jul. 26, 2023, which is hereby incorporated by reference in its entirety.

FIELD

Embodiments relates to a computer-implemented method for scattered radiation correction of a number of projection images of an x-ray imaging and to a computer-implemented method for parameterization, by machine learning, of a determination algorithm that serves to determine a measure of quality.

BACKGROUND

When x-rays are emitted part of the intensity arising at the detector is caused by scattered radiation. The scattered radiation received leads to a relatively even, varying additional intensity distribution, through which the image contrast is reduced. It is therefore desirable to reduce the influence of the scattered radiation on the imaging. The influence of scattered radiation is especially strong in cone beam computed tomography, for example. However other x-ray-based imaging methods may also profit when the influence of scattered radiation on the imaging is reduced.

For reducing the influence of the scattered radiation, a suitable design of the imaging facility may be used. For example, anti-scatter grids are used as a rule in order to reduce the intensity of the scattered radiation falling on the detector.

However, a part of the desired straight-line x-ray radiation passing through the examination object is also absorbed by an anti-scatter grid so that, to reach the same image quality, higher doses are required under some circumstances. For further improvement of the image quality or in order to make possible examinations with lower radiation doses, it may therefore be desirable to do without anti-scatter grids. Imaging without anti-scatter grids is for example highly relevant in the field of companion imaging for neurovascular interventions.

For imaging without an anti-scatter grid or also to complement the use of an anti-scatter grid the influence of scattered radiation may be reduced by a downstream processing of the measurement data. Approaches for this, that directly make use of an algorithm trained by machine learning, that processes captured image data as input data in order to generate image data with a smaller amount of scattered radiation, and approaches that are based on a direct solution of the Boltzmann transport equation, are to date sensitive to even small errors in the imaging model and are very processor-intensive.

Successful empirical or heuristic methods, that are based on the fact that the intensity distribution in the projection image resulting from the scattered radiation is a low-frequency function of the primary radiation captured are already being used in everyday clinical practice. In these approaches, to estimate the scattered radiation distribution, a convolution of the input image with a predetermined convolution kernel may be used. What is involved here however is a relatively rough approximation of the scattered radiation distribution, with which typically no optimum suppression of the proportion of scattered radiation in the image data may be achieved.

An estimation of the scattered radiation distribution with higher accuracy is possible with suitable prior knowledge, for example when fan beam computed tomography is available, that is at least largely free from disruption by scattered radiation. The appropriate prior knowledge is however not present in all relevant application cases.

The publication by Trapp, P. et al., Empirical scatter correction: CBCT scatter artifact reduction without prior information, Med Phys., Volume 49, Issue 7, July 2022, Pages 4566-45841, proposes to pre-specify an assumed scattered radiation distribution as the weighted sum of low-frequency basic images, wherein the weighting of the individual basic images is determined by an optimization method. Within the framework of this optimization method a weighted sum of the basic images with assumed weights is subtracted from the respective projection image in each case. On the basis of the projection images corrected in this way a three-dimensional image dataset is generated and a cost function is computed for the three-dimensional image dataset, that depends on the values of individual voxels in the three-dimensional image dataset. Then, with the aid of this cost function, an optimal weighting for the basic images is determined by a downhill simplex method.

BRIEF SUMMARY AND DESCRIPTION

The scope of the embodiments is defined solely by the appended claims and is not affected to any degree by the statements within this summary. The present embodiments may obviate one or more of the drawbacks or limitations in the related art.

Embodiments specify a computer-implemented method for scattered radiation correction, in which for example little or no prior knowledge is needed, with which a high image quality is achieved, and that is especially able to be implemented with little computing effort.

A computer-implemented method is provided for scattered radiation correction of a number of projection images of an x-ray imaging, that includes the following steps: obtaining the projection images, optimizing a measure of quality by variation of correction parameters used within the framework of the scattered radiation correction as a function of the projection images to determine optimal correction parameters, wherein a determination algorithm, that serves to determine the measure of quality, is an algorithm that is trained by machine learning and that processes a reconstructed three-dimensional image dataset or processing data that is selected from the image dataset and/or determined as a function of the image dataset, as input data, wherein the image dataset is based on corrected projection images, wherein the respective corrected projection image results from application of a correction algorithm to one of the projection images obtained in each case, wherein the correction algorithm is parameterized in each case by the correction parameters or by a subgroup of the correction parameters assigned to the respective projection image obtained, and provision of radiation scatter-corrected projection images by application of the correction algorithm to the respective projection image obtained, wherein the correction algorithm is parameterized in each case in accordance with the optimal correction parameters or the subgroup of the optimal correction parameters assigned to the projection image obtained in each case, and/or of a radiation scatter-corrected reconstructed three-dimensional image dataset, that is based on the radiation scatter-corrected projection images.

A number of advantages may be obtained by using a determination algorithm trained by machine learning for determination of the measure of quality. Compared to the method explained at the outset, in which for quality assessment voxel values are compared with ranges of setpoint values, less of a processing outlay is achieved, for example when, as will be explained below, by suitable selection or determination of the processing data, the amount of data to be processed is greatly reduced. It has namely been recognized that by using a determination algorithm trained by machine learning, even with a marked reduction in the amount of input data, a robust quality assessment may still be achieved to a large extent. Thus, for example, even with a limited amount of computing power available, an imaging almost in real time or with a short processing time may be achieved.

Through algorithms trained by machine learning frequently there is able to be differentiation as regards a variation of their input data, for example when, within the framework of machine learning there is to be back propagation with a gradient descent method. If in this case a correction algorithm is used, in which the change in the image values of the corrected projection images is able to be differentiated with regard to the correction parameters, that is the case as a rule for expedient correction algorithms, for which examples will be explained later, then the measure of quality with regard to the contour parameters is also able to be differentiated. This provides efficient optimization methods, for example the gradient descent method, to be used for determining the optimal correction parameters.

An algorithm trained by machine learning maps cognitive functions that humans associate with other human brains. Through training based on training data (machine learning) the trained algorithm is capable of adapting to new circumstances and detecting and extrapolating patterns.

Parameters of a trained algorithm may be adapted through training. For example, supervised learning, semi-supervised learning, unsupervised learning, reinforcement learning and/ or active learning may be used. Representation learning (also known as "feature learning") may be employed. The parameters of the trained algorithm may for example be adapted iteratively by a number of training steps.

A trained algorithm may for example include a neural network, a support vector machine (SVM), a decision tree, and/or a Bayes network and/or the trained algorithm may be based on k-means clustering, Q learning, genetic algorithms, and/or assignment rules. For example, a neural network may be a deep neural network, a convolutional neural network (CNN), or a deep CNN. The neural network may be an adversarial network, a deep adversarial network, and/or a generative adversarial network (GAN).

The optimization of the correction parameters may be carried out for example for a predetermined number of iterations. A convergence criterion is checked, of which the fulfillment is for example dependent on a comparison between the resulting measure of quality for the correction parameters last used and a predetermined limit value.

The training of the algorithm by machine learning may be carried out as part of the method, however it is also possible for the training to precede the method and not to be a part of the method, so that the method begins with an already trained algorithm. Suitable approaches to training the algorithm will be explained in greater detail later with regard to the training method.

The determination algorithm may exclusively process the processing data as input data. The processing data is formed by a number of two-dimensional slice images spaced apart from one another and/or oriented at an angle to one another in each case or by precisely one two-dimensional slice image of the three-dimensional image dataset.

By an evaluation of two-dimensional slice images instead of three-dimensional image data the amount of input data processed may be significantly reduced. If for example a neural network is used as a determination algorithm, this provides the number of the required nodes of the input layer and thus also the number of nodes of subsequent layers to be greatly reduced. The computing power required and the memory requirement for executing the determination algorithm may be reduced. The smaller number of nodes also leads to a smaller number of free parameters. A smaller number of training data and less computing power is required for the training of the neural network. Similar advantages as regards the reduction in the scope of the input data also result with other algorithms that are able to be trained by machine learning.

For example, slice images in axial and/or coronal and/or sagittal slice planes may be considered as processing data.

The requirement for the various slice images to be at an angle to one another and/or spaced apart from one another applies to each pair of slice images from the processing data. The image data of the slice images may correspond directly to the values of the voxels within the selected slice, but may for example also be determined by interpolation, for example for angled slice images or with a scaling of the slice images with regard to the three-dimensional image data.

As an alternative or in addition to the use of slice images as processing data, there may also for example be a downsampling of the three-dimensional image data for resolution reduction to reduce the amount of the input data.

The correction algorithm may include the determination of an estimated scattered radiation distribution for the respective projection image obtained depending on the correction parameters or on the subgroup of correction parameters assigned to the respective projection image obtained, wherein the corrected projection image may be determined by subtraction of the estimated scattered radiation distribution from the projection image obtained.

It may thus be assumed that the projection images obtained may be considered at least approximately as the sum between scattered-radiation-free projection images and an overlaid scattered radiation distribution. This provides a simple and robust scattered radiation correction to be achieved. The scattered radiation distribution may, apart from the choice of the correction parameters, be independent of the x-ray projection images obtained. The scattered radiation distribution may depend exclusively indirectly via the correction parameters on the x-ray projection images.

The scattered radiation distribution may be determined as a weighted sum of basic images. The weighting factors with which the basic images are weighted in the weighted sum are predetermined by the correction parameters or by the subgroup of the correction parameters assigned to the respective projection image obtained.

The basic images or at least a few of the basic images may be permanently predetermined and for example depict various B splines and/or Gaussian distributions. In addition, or as an alternative at least a few basic images may depict periodic basic functions, for example planar sine and/or cosine waves.

In addition, or as an alternative at least one of the basic images may be predetermined as a function of at least one of the correction parameters. The instances of the respective basic image resulting from a different choice of correction parameter are able to be transferred into each other by an affine transformation or by a number of affine transformations applied after one another.

For example, the various instances of the respective basic image may be generated by an affine transformation, that is parameterized by the at least one correction parameter, from a common original image. If all basic images are generated by at least one affine transformation from a common image or from a number of common images, the scattered radiation distribution may for example be generated as the weighted sum of affine transformed original images in each case.

The condition that instances of the respective basic image are able to be transferred into one another by an affine transformation or by a number of affine transformations applied after one another may, as an alternative or in addition, also be fulfilled when the basic image is created by a parameterization of a function generating the basic image, for example a two-dimensional Gaussian curve or a two-dimensional B spline.

An affine transformation is understood in this context for example as a rotation and/or a scaling and/or a shearing and/or a convolution.

The scattered radiation distribution or at least a respective one of the basic images and/or at least one respective original image on the basis of which a respective one of the basic images is determined, may be predetermined by a two-dimensional Gaussian distribution and/or a two-dimensional B spline. At least one parameter of the respective Gaussian distribution and/or of the respective B spline is predetermined by a respective one of the correction parameters. These functions are well suited to modeling or for at least approximately emulating actual scattered radiation distributions occurring.

The determination algorithm used in the method explained may be trained by supervised learning. In principle training datasets may be used for this, that each include a three-dimensional image dataset or, as explained above, image processing data, for example at least one slice image, and an assigned setpoint measure of quality. Then, as part of the training, the deviation between the measure of quality determined by the determination algorithm for a specific image dataset or for specific processing data and the assigned setpoint measure of quality is minimized, for example by a back propagation being carried out in order to determine parameters of the determination algorithm, for example node-weighted in a neural network. This type of training of an algorithm by machine learning is sufficiently known from other areas of application and will thus not be explained in detail here.

The predetermination of corresponding setpoint measures of quality for three-dimensional image data already affected by scattered radiation or of processing data, for example manually by an expert, is however expensive and potentially susceptible to errors. Therefore, a better approach to parameterization of the determination algorithm by machine learning is to be specified.

Embodiments provide a computer-implemented method for parameterization of a determination algorithm, that serves for determination of a measure of quality, for example in the computer-implemented method for scattered radiation correction by machine learning, that includes the following steps: specification of a number of training datasets, which each include a number of pairs consisting of a reference projection image and a scattered radiation distribution assigned to the respective reference projection image, generation of a respective intermediate image, in that the assigned value of the assigned scattered radiation distribution is added in each case to the image values of the image points of the respective reference projection image, determination of a proportion of scattered radiation for the respective training dataset depending on the image values of the reference projection images of the training dataset and the assigned value of the assigned scattered radiation distribution in each case, minimization of a cost function, that depends on the respective deviation between a measure of quality determined by the determination algorithm and the proportion of scattered radiation for the number of training datasets, by variation of a number of parameters of the determination algorithm for determination of an optimal parameter set for the parameters of the determination algorithm, wherein the determination algorithm processes a reconstructed three-dimensional image dataset or processing data, that is chosen from the image dataset and/or is determined as a function of the image dataset, as input data, wherein the image dataset is based on the intermediate images.

The optimal parameter set and/or the parameterized determination algorithm may be provided, stored for later use and/or used directly.

The method provides the proportion of scattered radiation used as the setpoint measure of quality to be determined in an automated manner and precisely. For example, the proportion of scattered radiation may be calculated by the assigned value of the assigned scattered radiation distribution being divided by the image value of the image point of the reference projection image for the respective image point of the respective reference projection image in order to determine a proportion of scattered radiation for the respective image point. The proportion of scattered radiation for the entire intermediate image may then be calculated in each case by the proportions of scattered radiation of all image points of the reference projection image underlying the respective intermediate image being added, after which there may be a normalization, for example by a division by the number of image points being carried out.

The reference projection images of the respective training dataset may depict the same examination object or the same region for different projection directions, so that in principle three-dimensional image data of the examination object or of the region depicted may be reconstructed from the reference projection images of the training dataset.

The reference projection images may be predetermined in such a way that no scattered radiation is depicted in them or the influence of the scattered radiation in them is negligible. This may be achieved for example by an imaging being undertaken by a simulation on the basis of a predetermined three-dimensional image dataset.

The simulation may be performed for example by Monte Carlo approaches or by a direct solution of the Boltzmann transport equation. In a simulation of the imaging, amounts of scattered radiation may be recognized and discarded or provided separately as the assigned scattered radiation distribution.

As an alternative or in addition suitable reference projection images may be provided for example by suitable imaging facilities, for example by using an anti-scatter grid, and/or by postprocessing of the measurement data, for example by computing-intensive methods for scattered radiation reduction.

At least parts of the training datasets may include groups of reference projection images that differ from one another. The different groups may depict different regions of examination objects.

In addition, or as an alternative, at least parts of the training datasets may differ from one another exclusively with regard to the scattered radiation distributions. In one case the number of training datasets may be increased by the same reference images and by differently scaled scattered radiation distributions being used in various training datasets. It is for example possible however, in addition or as an alternative, to change scattered radiation distributions by an affine transformation or the like between various training datasets.

For at least one of the training datasets the reference projection images and a provisional scattered radiation distribution assigned to the respective reference projection image may be obtained by simulation of an image of a predetermined three-dimensional reference dataset. The scattered radiation distribution contained in the training dataset assigned to the respective reference projection image may be predetermined by a scaling and/or an affine transformation of the provisional scattered radiation distribution.

A scaling is to be understood for example as a scaling of the values of the scattered radiation. A change in size of the image size of the scattered radiation distribution is possible, in addition or as an alternative, via a corresponding affine transformation.

For example, the same reference projection image may be used in a further of the training datasets and the provisional scattered radiation distribution may be used directly as the control radiation distribution. In addition, or as an alternative, the same reference projection image may be used in at least one of the further training datasets and the assigned scattered radiation distribution may likewise be predetermined by a scaling and/or affine transformation of the provisional scattered radiation distribution, wherein however another parameterization of the scaling and/or of the affine transformation is used.

Through the described procedure it is made possible that simulated scattered radiation distributions may be used, for which it may be assumed that they are a good match to the scattered radiation distributions that really occur. At the same time however, by use of the scaling or of the affine transformation, the number of training datasets available for training is increased, with which through the trained algorithm, even with deviations from the expected or simulated scattered radiation distribution, the measure of quality, that for example corresponds at least approximately to a proportion of scattered radiation, may be robustly determined.

A first of the scattered radiation distributions may be predetermined as a weighted sum of a number of predetermined two-dimensional distribution functions with first weighting factors, wherein a second of the scattered radiation distributions is predetermined as the weighted sum of the predetermined two-dimensional distribution functions with second weighting factors, that are different from the first weighting factors.

The first and second scattered radiation distribution may be part of the same training dataset, for example in order to provide a training dataset with different scattered radiation distributions for different projection directions. In addition, or as an alternative the first and second scattered radiation distribution may be assigned for example in different training datasets to the same reference projection image in order to simulate different possible scattered radiation distributions for the same projection image.

The creation of synthetic scattered radiation distributions by differently weighted sums of predetermined distribution functions is expedient when an actual scattered radiation distribution assigned to the respective reference projection image is unknown. This process is also expedient however in order to provide a greater number of training datasets. Randomly chosen combinations or weightings of the distribution functions may be overlaid for this purpose for example.

Through a suitable choice of the distribution functions taken into account, scattered radiation distributions may for example also be generated that, although they are not likely to occur in measurement data, may however occur in the corrected projection image within the framework of the method for scattered radiation correction mentioned above, whereby it is expedient to also take account of scattered radiation distributions as part of the training.

A periodic function, for example at least one sine function and/or at least one cosine function, may be used as at least one of the distribution functions. The two-dimensional function used may have the same or also different periodicity in orthogonal space directions. For example, a number of distribution functions with different periods and/or phase positions and/or orientations from one another may be used, that may be overlaid in the weighted sum.

It has been recognized that at least the additional taking into account of periodic functions as the distribution function within the framework of a weighted sum is especially well suited for taking account of scattered radiation distributions that may occur within the framework of the optimization of the scattered radiation correction mentioned above, that however typically do not occur in measurement data during training.

The period length of the periodic function may be at least a fifth or at least a third of the image height and/or the image width of the reference projection image assigned to the respective scattered radiation distribution. For example, the period length may be between half and twice the image width or image height. To put it differently, low-frequency periodic functions may be used for modeling the scattered radiation distribution, since no radio-frequency components typically occur in the scattered radiation distribution.

In addition, or as an alternative, at least one of the distribution functions used may stem through an affine transformation from a distribution function generated by a periodic function. For example, the phase position, the period and/or the alignment of the distribution function may be adapted by a suitable affine transformation.

In addition, or as an alternative at least one Gaussian distribution and/or at least one B spline and/or at least one scattered radiation distribution determined within the framework of the simulation and/or an affine transformation of one of the possible distribution functions may also be used as the distribution function.

In an embodiment a first of the scattered radiation distributions is predetermined as the predetermined two-dimensional distribution function or as the weighted sum, that includes the predetermined two-dimensional distribution function as a summand, wherein a second of the scattered radiation distributions is predetermined as an affine transformation of the predetermined two-dimensional distribution function or as the weighted sum, that includes the affine transformation of the predetermined two-dimensional distribution function as a summand. The first and second scattered radiation distribution may correspond to the first and second scattered radiation distribution mentioned above or also be different from these. The first and second scattered radiation distribution may be part of the same training dataset or be from different training datasets, wherein for example they may be assigned in different training datasets to the same reference projection image.

For example, at least a few of the scattered radiation distributions may be predetermined as the weighted sum of affine transformations of different predetermined distribution functions and/or as the weighted sum of different affine transformations of the same distribution function. The distribution function for which an affine transformation is undertaken may for example be determined by a simulation, as has been explained above.

As well as the method, embodiments provide a data processing facility, that is configured to carry out the computer-implemented method for scattered radiation correction and/or to carry out the computer-implemented method for parameterization of a determination algorithm.

The data processing facilities may include an input interface for obtaining the projection images and/or the training datasets and/or data on which the training datasets are based. In addition, or as an alternative the data processing facility may include an output interface for provision of the radiation scatter-corrected projection images and/or of the radiation scatter-corrected reconstructed three-dimensional image dataset and/or of the optimal parameter set and/or of the parameterized determination algorithm.

The data processing facilities may for example be integrated into a medical imaging facility, for example into a cone beam topograph, or be configured as separate data processing facilities, for example as a workstation or server. As an alternative it is also possible however to implement the data processing facilities as a cloud solution.

For implementation of the data processing facilities for example a microprocessor, an FPGA, a microcontroller, a graphics processor, or similar may be used, that is configured by suitable programming for carrying out the method or methods. As an alternative the data processing facilities may however also be implemented by an application-specific integrated circuit or generally be hard wired.

Embodiments provide a computer program including instructions that are configured, when executed on a data processing facility, to carry out the computer-implemented method for scattered radiation correction and/or the computer-implemented method for parameterization of a determination algorithm.

Embodiments provide a data medium, that includes a computer program.

The features explained for an embodiment may also be transferred with the advantages to other of the embodiments.

BRIEF DESCRIPTION OF THE FIGURES

FIG. 3 depicts relevant algorithms and data structures in an embodiment of the method for parameterization of a determination algorithm.

DETAILED DESCRIPTION

Figure 1:
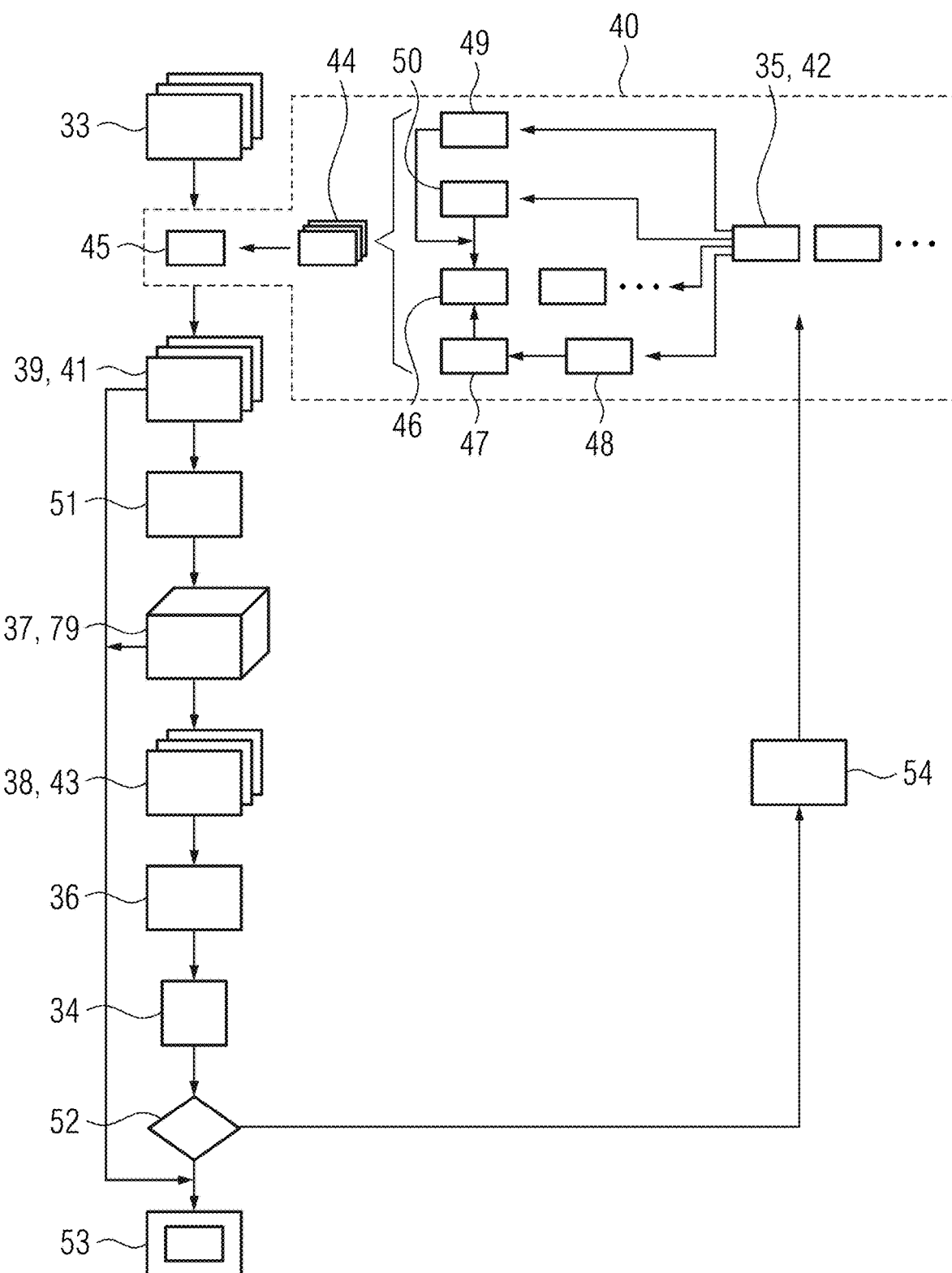
FIG. 1 depicts relevant algorithms and data structures in an embodiment of the method for scattered radiation correction.
Figure 2:
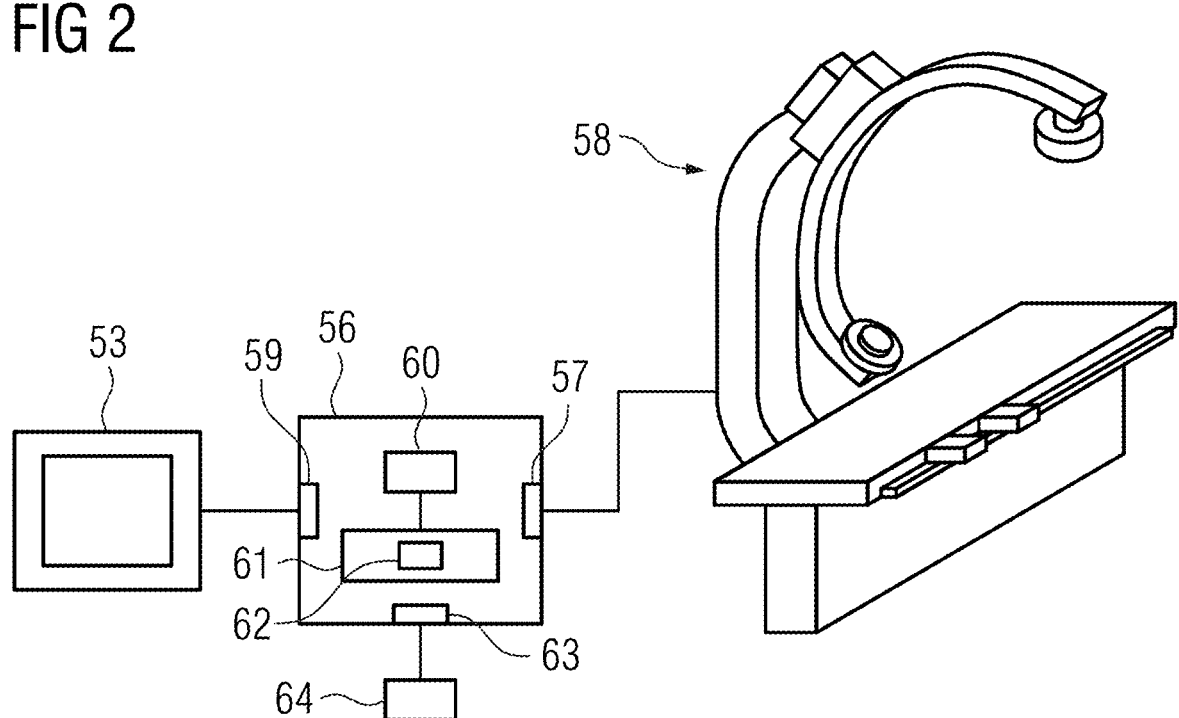
FIG. 2 depicts an embodiment of the data processing facility.

FIG. 1 depicts relevant algorithms and data structures for the implementation of a computer-implemented method for scattered radiation correction of a number of projection images 33 of an x-ray imaging. For x-ray imaging for example the C-arm facility 58 as shown in FIG. 2 may be used, that may record projection images 33 from different perspectives, from which, for example within the framework of cone beam tomography, a three-dimensional image dataset may be reconstructed. This may for example also be used between operations or generally for a real-time visualization, by for example specific sections or slice planes being shown on a display facility 53.

It may be expedient to record corresponding projection images 33 without an anti-scatter grid or at least, in addition to scattered radiation suppression by the anti-scatter grid, to carry out a downstream scattered radiation correction of the projection images 33 acquired or provided to the method.

In the method, the projection images 33, for which a scattered radiation correction is to take place, are obtained. In the example shown in FIG. 2 this is undertaken directly by the imaging facility via an input interface 57 of the data processing facility 56, that implements the method. This is expedient for example for a real-time visualization. As an alternative the projection images 33 may however also be taken from a database or from any other given data source independently of the measurement data acquisition.

The scattered radiation correction is carried out by a measure of quality 34 being optimized, that for example is intended to be a measure for a proportion of scattered radiation in the projection images 33. What is significant here however is that the determination algorithm 36, that determines this measure of quality 34, does not operate on projection images, but on a reconstructed three-dimensional image dataset 37 or on processing data 38 determined from this and that the determination algorithm 36 is trained by machine learning. A possible approach to implementation of such machine learning will be explained later with reference to FIG. 3.

Thus, within the framework of the optimization, corrected projection images 39 are thereby determined first of all by a correction algorithm 40 on the basis of the projection images 33 obtained. The correction algorithm 40 is parameterized here by a number of correction parameters 35, that are varied within the framework of the optimization. Start values for the correction parameters 35 may be predetermined as fixed for example or may be specified at random.

Then, on the basis of the corrected projection images 39, a three-dimensional image dataset 37 is reconstructed by a reconstruction algorithm 51. Any reconstruction algorithm that is suitable for reconstruction of three-dimensional image data from x-ray projection images may be used as a reconstruction algorithm 51. For example, a filtered back projection, an iterative reconstruction or similar may be used.

In principle the determination algorithm 36, that specifies the measure of quality 34 for the respective iteration of the optimization, may be applied directly to the three-dimensional image dataset 37. As has already be explained in the general part, it is advantageous however to reduce the amount of input data that must be processed by the determination algorithm 36. Therefore, in the example, first of all processing data 38 is selected, namely a number of individual slice images 43, that relate to slices that are spaced apart from one another or are at an angle to each other in the imaged volume, from the three-dimensional image dataset 37, and are used as input data for the determination algorithm 36.

After the determination of the measure of quality 34 by the determination algorithm 36 a convergence condition 52 is checked. For example, a check may be made as to whether the measure of quality 36 and thus in the example a remaining proportion of scattered radiation in the corrected projection image data 39 falls below a limit value.

If this is the case, then the scattered radiation correction is already concluded and the correction parameters 35 last used correspond to the optimal correction parameters 42. The corrected projection images 39 last determined may thus be output directly as radiation scatter-corrected projection images 41 via the output interface 59 shown in FIG. 2 to the display facility 53.

In addition, or as an alternative the three-dimensional image dataset 37 last reconstructed may be output as the radiation scatter-corrected reconstructed three-dimensional image dataset or further processed after its provision, for example in order to show specific slice planes on the display facility 35.

Via the operator interface 63, likewise shown in FIG. 2, and by an operation 64 connected thereto it may be chosen for example that projections or sections are to be displayed via the display facility 53.

If the convergence condition 52 is not fulfilled on the other hand, then the correction parameters 35 used by the optimization algorithm 54 are changed in the correction algorithm 40, after which the determination of the measure of quality 34 is repeated. This is now carried out however on the basis of corrected projection images 39, that have been determined with the changed correction parameters 35.

There is a wide variety of known approaches for an iterative adjustment of parameters in an optimization method. In the example shown use may for example be made of the fact that the algorithm 36 for determination of the measure of quality 34 trained by machine learning and the correction algorithm 40 are able to be differentiated, so that a derivation of the measure of quality 34 is able to be calculated according to the individual correction parameters 35 and thus for example a gradient descent method known per se may be used for parameter adjustment.

The correction algorithm 40 is based in the example on a scattered radiation distribution 44 being estimated for the respective projection image 33 obtained or being predetermined on the basis of the correction parameters 35, after which the estimated scattered radiation distribution 44 is subtracted 45 from the respective projection image 33 obtained in order to provide the respective corrected projection image 39.

Separate correction parameters may be used in the correction algorithm 40 for correction of the individual projection images 33, so that a subgroup of the correction parameters 35 may be assigned to the individual production image 33 obtained. In this case the respective estimated scattered radiation distribution 44 is predetermined on the basis of this subgroup and subtracted from the respective projection image 33 within the framework of the correction.

In the example shown the respective scattered radiation distribution 44 is determined as the weighted sum of basic images 46, wherein the weighting factors are predetermined by the respective subgroup of the correction parameters 35. For example, the respective subgroup of the correction parameters 35 may include a correction parameter 35 assigned to the respective basic images 46 as a weighting factor.

Figure 4:
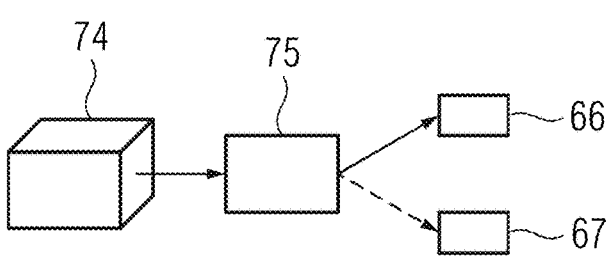
FIGS. 4 and 5 depict examples of embodiments of the determination of the reference projection images and scattered radiation distributions used in FIG. 1.

In one case the predetermination of all basic images 46 may be fixed. Examples for suitable basic images 46 have already been discussed above. In the example however at least parts of the basic images 46 are predetermined in another way. A scattered radiation distribution, that was previously determined by a simulation method, as will be discussed in more detail below with reference to FIG. 4, is used as the original image 48, that is modified additionally by an affine transformation 47, for example by a rotation, distortion and/or shearing, and/or may optionally be scaled in order to provide one of the basic images 46. The affine transformation 47 or scaling is likewise undertaken as a function of at least one correction parameter of the subgroup of correction parameters, for example by an angle of rotation and/or scaling factor predetermined as a correction parameter.

In the example parts of the basic images 46 are moreover provided by a two-dimensional Gaussian distribution 49 and a two-dimensional B spline 53 being parameterized by respective correction parameters 35.

The specified process for determination of the respective estimated scattered radiation distribution 44 is by way of example. In the general part numerous further formation options for the scattered radiation distribution 44 depending on the correction parameters 35 have already been explained. For example, it would be possible to provide the estimated scattered radiation distribution exclusively by a parameterization of a Gaussian distribution 49 or of a B spline 50 or by a parameterization of the affine transformation 47 and thus to dispense with the formation of a weighted sum. As an alternative, affine transformations could be applied generally, additionally or as an alternative to sum formation, to all basic images. It would also be possible for example to predetermine just one basic image and exclusively to scale this and/or subject it to an affine transformation for provision of the estimated scattered radiation distribution.

The method explained may be implemented for example by the data processing facilities 56 shown in FIG. 2. This includes a programmable processor 60 and a memory 61, in which a computer program 62 is stored, of which the instructions implement the explained method and, in addition or as an alternative, the training method explained below with reference to FIG. 3.

Figure 3:
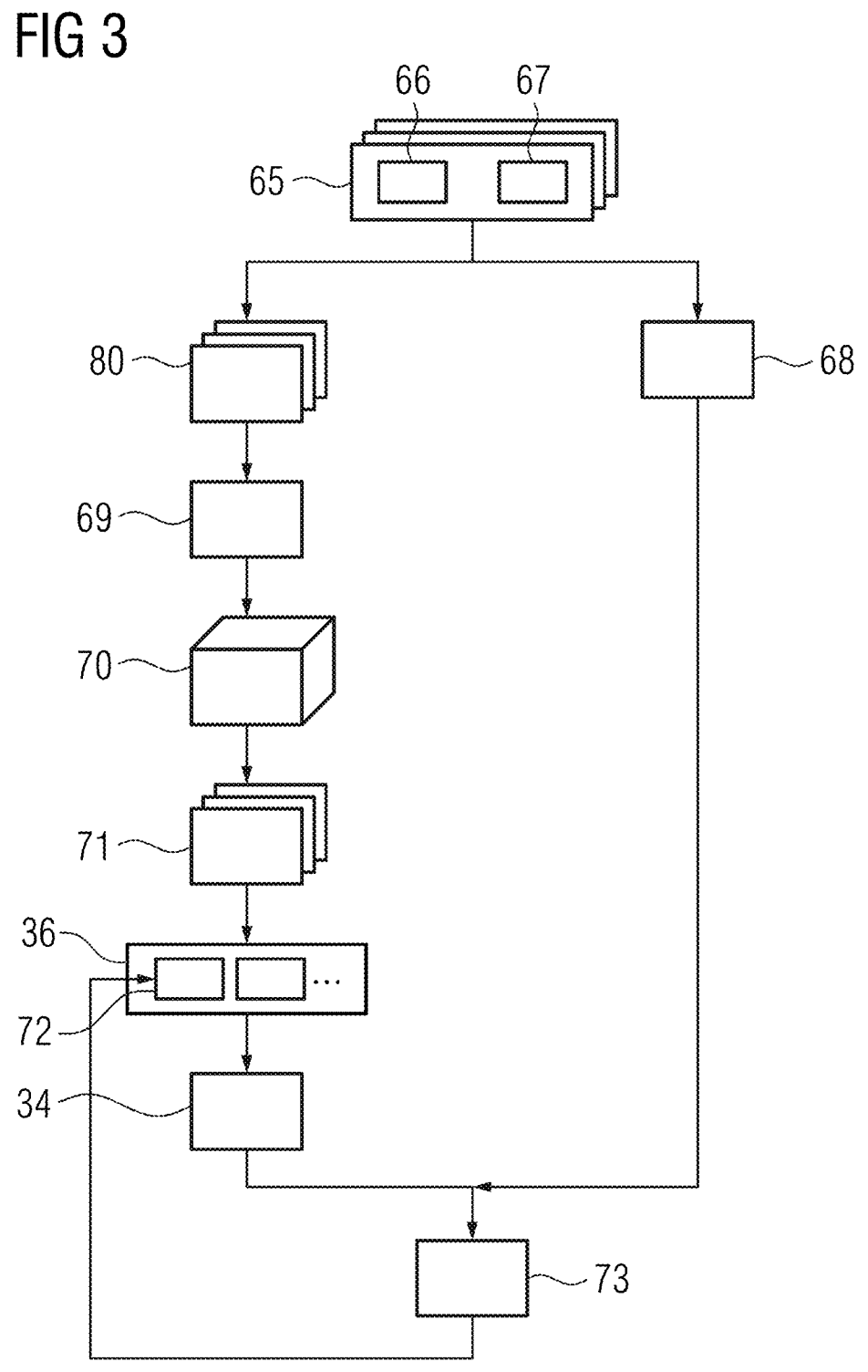

FIG. 3 depicts relevant algorithms and data structures of a method for parameterization of a determination algorithm 36, that may be used for example as a determination algorithm in the method explained previously with reference to FIG. 1, by machine learning. Training datasets are used as input data of the method, which each include a number of pairs 65 consisting of a respective reference projection image 66 and a scattered radiation distribution 67 assigned to the respective reference projection image. For reasons of clarity only the pairs 65 of one of the training datasets are shown in FIG. 3.

Projections of the same examination object or examination volume from different perspectives may be used as reference projection images 66 of the respective training dataset, so that in principle a three-dimensional representation of the examination object or of the examination volume may be reconstructed from the reference projection images 66.

The reference projection images 66 may be essentially free from intensity contributions by scattered radiation. This may be achieved for example by the reference projection images 66 being acquired with a suitable imaging geometry, for example by using anti-scatter grids.

As shown schematically in FIG. 4, a simulation 75 may be used in order to depict a predetermined three-dimensional reference dataset 74. A Monte Carlo approach may be used for simulation for example or the transport equation for the x-ray radiation may be solved. Corresponding simulation approaches make it possible for x-ray quanta falling on the simulated detector to distinguish between scattered radiation and direct x-ray radiation, so that, directly as the result of the simulation 75, pairs consisting of reference projection images 66 and assigned scattered radiation distributions 67 may be predetermined. Since the scattered radiation distribution 67 determined by the simulation 75 may still be modified before it is used in a respective training dataset, it may also be considered as a provisional scattered radiation distribution 67.

In order to increase the number of the training datasets and thus achieve a more robust training, it is possible that, for provision of a further training dataset, the same reference projection images 66 created by the simulation 75 are used, but the assigned scattered radiation distributions 67 are created synthetically. Such a synthetic creation of scattered radiation distributions 67 may also be expedient when the reference projection images 66 are determined by measurements, since in these cases frequently no information is available about the actual scattered radiation distribution.

Figure 5:
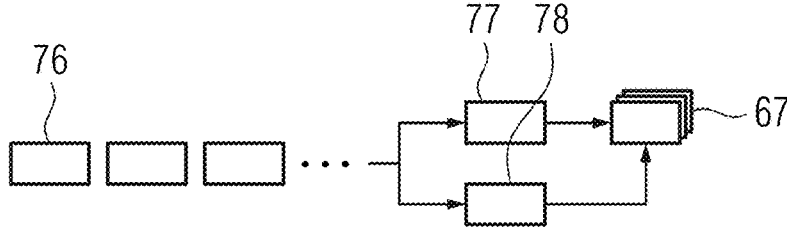

One possibility for provision of scattered radiation distributions 67, that may be used as part of the training datasets, will be explained below with additional reference to FIG. 5. In this example a plurality of distribution functions 76 is predetermined. The respective scattered radiation distribution 67 is predetermined by a weighted sum 77 of the distribution functions 76 or by an affine transformation 78 of one of the distribution functions 76.

By different choice of the weighting factors or of the parameters of the affine transformation 78, for example by use of different angles of rotation, a plurality of different scattered radiation distributions 67 and thus a plurality of training datasets may be generated. The use of affine transformations 78 of individual distribution functions 76 and of a weighted sum 77 may also be combined in order to generate a weighted sum of affine transformed distribution functions 76 in each case as scattered radiation distribution 67.

Periodic functions, for example a sine or cosine function, with relatively large period length may be used as distribution functions 76, since these are well suited, by overlaying, to emulate a typically pure low-frequency actual scattered radiation distribution.

By suitable, for example random, overlaying of such distribution functions 76 robust measures of quality or proportions of scattered radiation may then be determined, if, within the framework of the optimization explained in FIG. 1, scattered radiation distributions in the corrected projection image result that would not arise in actual measurements.

The summation, scaling and/or affine transformation of two-dimensional distribution functions 76 for provision of a scattered radiation distribution explained with reference to FIG. 5 may also be used for modification of a scattered radiation distribution 67, that, as is shown in FIG. 4, was created by a simulation 75. For example, the scattered radiation distribution 67 created by the simulation 75 may be rotated and/or scaled for use in a further training dataset and/or it may be summed weighted with at least one further distribution function 76.

After the specification of the training datasets intermediate images 80 are generated for the respective training dataset, by the assigned value of the assigned scattered radiation distribution 67 of the same pair 65 being added in each case to the image values of the image points of the respective reference projection image 66. The intermediate images thus correspond to projection images that are disrupted by the respective scattered radiation distribution 67.

Subsequently a three-dimensional image dataset 70 is reconstructed on the basis of the intermediate images 80 by a reconstruction algorithm 69. This corresponds at least essentially to the use of the reconstruction algorithm 51 in FIG. 1.

Processing data 71, i.e. for example individual slices, is extracted from the three-dimensional image dataset 70, as has already been explained with reference to FIG. 1, in order to reduce the amount of input data of the determination algorithm 36 to be trained. The processing data 71 is then conveyed to the determination algorithm 36 initially parameterized with an initial parameterization in order to determine a measure of quality 34.

Parallel to the determination of the measure of quality 34 a proportion of scattered radiation 68 for the respective training dataset is determined as the setpoint value for the measure of quality 34. For this purpose, the quotient from the value assigned to the image point of the assigned scattered radiation distribution 67 and the image value of this image point is calculated for each image point of each reference projection image 66 of each pair 65 of the training dataset in each case and a summation is carried out over all image points and optionally a subsequent normalization, for example by division of this value by the number of image points taken into consideration.

Depending on a cost function 73, that in the example is the sum of the deviations of the measures of quality 34 from the proportions of scattered radiation 68 over the training datasets, the parameters 72 of the determination algorithm 36, i.e. for example node weights of a neural network, are subsequently modified. This may be undertaken for example in accordance with the back propagation known from the area of machine learning. For example, a gradient descent method or similar may be used for minimization of the deviation or of the cost function 73. Thus, the algorithm 36 is trained to determine as the measure of quality at least approximately the proportion of scattered radiation 68 and is thus well suited for use in the method explained with reference to FIG. 1.

Figure 6:
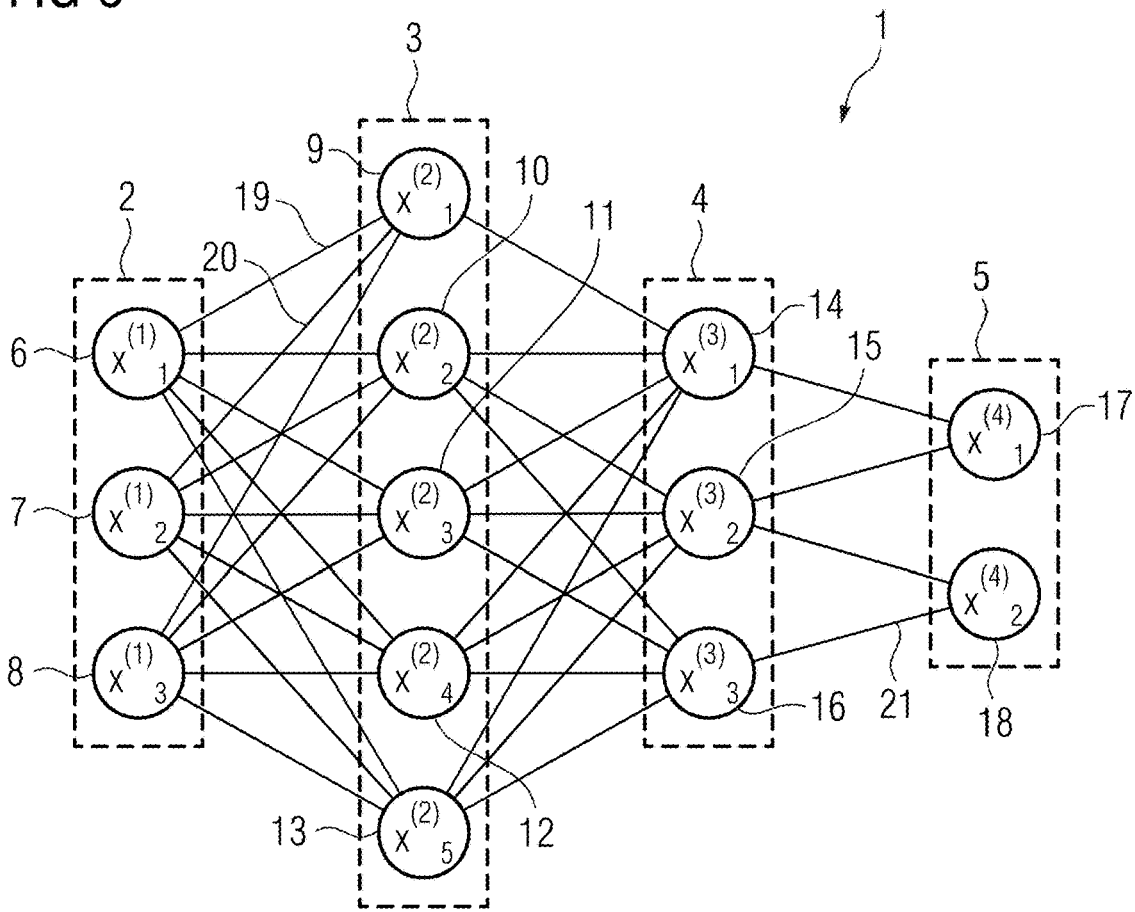
FIGS. 6 and 7 depict examples of possible embodiments for the determination algorithm trainable by machine learning to be used in FIGS. 1 and 3.
Figure 7:
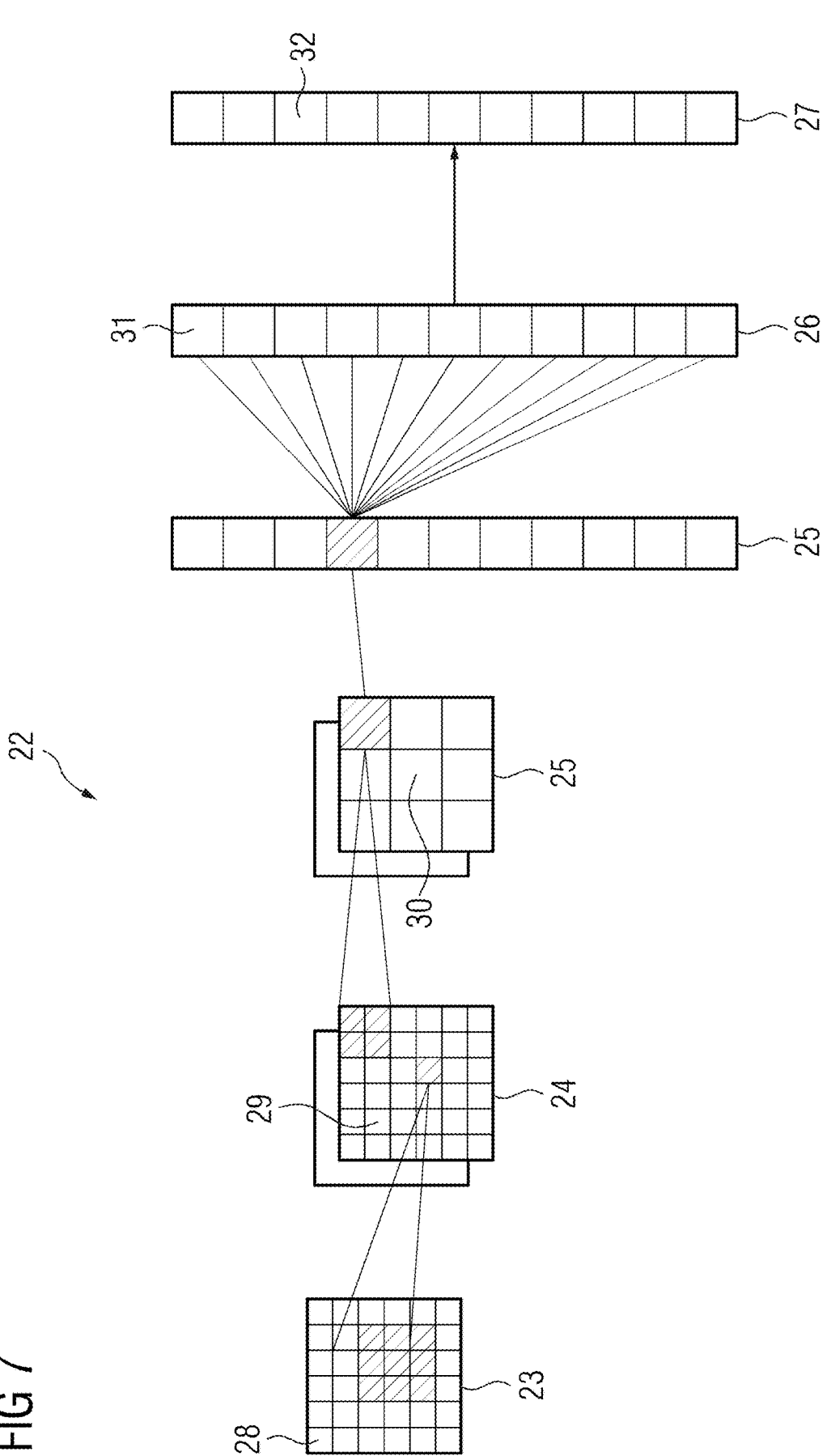

Examples of embodiments for the determination algorithm 36 able to be used in FIGS. 1 and 3, able to be trained by machine learning are shown in FIGS. 6 and 7. In the examples neural networks are used as algorithms to be trained. Examples of other trainable algorithms have already been given in the general part. Illustrated for reasons of clarity are networks with a relatively small number of nodes. Significantly larger numbers of nodes may be used.

FIG. 6 depicts an embodiment of an artificial neural network 1. Other expressions for the artificial neural network 1 are neural network, artificial neural net or neural net.

The artificial neural network 1 includes nodes 6 to 18 and edges 19 to 21. Each edge 19 to 21 is a directed connection from a first node 6 to 18 to a second node 6 to 18. The first node 6 to 18 and the second node 6 to 18 are different nodes 6 to 18, it is also conceivable however for the first node 6 to 18 and the second node 6 to 18 to be identical. For example, in FIG. 6 the edge 19 is a directed connection from the node 6 to the node 9 and the edge 21 is a directed connection from the node 16 to the node 18. An edge 19 to 21 from a first node 6 to 18 to a second node 6 to 18 is referred to as the ingoing edge for the second node 6 to 18 and as the outgoing edge for the first node 6 to 18.

In this embodiment the nodes 6 to 18 of the artificial neural network 1 may be arranged in layers 2 to 5, wherein the layers may have an intrinsic order, that is introduced by the edges 19 to 21 between the nodes 6 to 18. For example, edges 19 to 21 may only be provided between neighboring layers of nodes 6 to 18. In the embodiment shown an input layer 2 exists, that merely has the nodes 6, 7, 8, each without an ingoing edge. The output layer 5 includes only the nodes 17, 18, each without an outgoing edge, wherein hidden layers 3 and 4 further lie between the input layer 2 and the output layer 5. In the general case any number of hidden layers 3, 4 may be chosen. The number of nodes 6, 7, 8 of the input layer 2 usually corresponds to the number of input values in the neural network 1, and the number of nodes 17, 18 in the output layer 5 usually corresponds to the number of output values of the neural network 1.

For example, a (real) number may be assigned to nodes 6 to 18 of the neural network 1. In this case $x^{(n)}_i$ refers to the value of the ith node 6 to 18 of the nth layer 2 to 5. The values of the nodes 6, 7, 8 of the input layer 2 are equivalent to the input values of the neural network 1, while the values of the nodes 17, 18 of the output layer 5 are equivalent to the output values of the neural network 1. Each edge 19, 20, 21 may be assigned a weight in the form of a real number. For example, the weight is a real number in the interval $[-1, 1]$ or in the interval $[0, 1,]$. In this case $w^{(m,n)}_{i,j}$ refers to the weight of the edge between the ith node 6 to 18 of the mth layer 2 to 5 and the jth node 6 to 18 of the nth layer 2 to 5. The abbreviation $$w^{(n)}_{i,j}$$

is further defined for the weight $$w^{(n,n+1)}_{i,j}.$$

In order to calculate output values of the neural network 1, the input values are propagated through the neural network 1. For example, the values of the nodes 6 to 18 of the (n+1)th layer 2 to 5 may be calculated, based on the values of the nodes 6 to 18 of the nth layer 2 to 5, by $$x^{(n+1)}_j = f\left(\sum_i x^{(n)}_i \cdot w^{(n)}_{i,j}\right).$$

In this case f is a transfer function, that may also be referred to as an activation function. Known transfer functions are stage functions, sigmoid functions (for example the logistical function, the generalized logistical function, the hyperbolic tangent, the arc tangent, the error function, the smoothstep function) or rectifier functions. The transfer function is essentially used for normalization purposes.

For example, the values are propagated layer-by-layer through the neural network 1, wherein values of the input layer 2 are given by the input data of the neural network 1. Values of the first hidden layer 3 may be calculated based on the values of the input layer 2 of the neural network 1, values of the second hidden layer 4 may be calculated based on the values in the first hidden layer 3 etc.

In order to be able to define the values $$w^{(n)}_{i,j}$$

for the edges 19 to 21, the neural network 1 must be trained using training data. For example, training data includes training input data and training output data, that is referred to below as $t_i$. For a training step the neural network 1 is applied to the training input data in order to determine calculated output data. For example, the training input data and the calculated output data include a number of values, wherein the number is specified as the number of the nodes 17, 18 of the output layer 5.

For example, a comparison between the calculated output data and the training output data is used in order recursively to adapt the weights within the neural network 1 (back propagation algorithm). For example, the weights may be changed according to $$w'^{(n)}_{ij} = w^{(n)}_{i,j} - \gamma \cdot \delta^{(n)}_j \cdot x^{(n)}_i,$$

wherein $\gamma$ is a learning rate and the numbers $$\delta^{(n)}_j$$

may be calculated recursively as $$\delta^{(n)}_j = \left(\sum_k \delta^{(n+1)}_j \cdot w^{(n+1)}_{j,k}\right) \cdot f'\left(\sum_i x^{(n)}_i \cdot w^{(n)}_{i,j}\right)$$

based on $$\delta^{(n+1)}_j,$$

when the (n+1)th layer is not the output layer 5, and $$\delta^{(n)}_j = \left(x^{(n+1)}_k - t^{(n+1)}_j\right) \cdot f'\left(\sum_i x^{(n)}_i \cdot w^{(n)}_{i,j}\right)$$

if the (n+1)th layer is the output layer 5, wherein f is the first derivation of the activation function and $$y^{(n+1)}_j$$

is the comparison training value for the jth node 17, 18 of the output layer 5.

Provided below in respect to FIG. 7 is also an example of a convolutional neural network (CNN). In this case it is to be noted that the expression "layer" is used there in a slightly different manner to how it is used for classical neural networks. For a classical neural network, the expression "layer" only refers to the set of nodes that forms a layer, thus to a specific generation of nodes. For a convolutional neural network, the expression "layer" is often used as an object that actively changes data, in other words as a set of nodes of the same generation and either the set of ingoing or outgoing edges.

FIG. 7 depicts an embodiment of a convolutional neural network 22. In the embodiment shown the convolutional neural network 22 includes an input layer 23, a convolutional layer 24, a pooling layer 25, a fully connected layer 26 and an output layer 27. In alternative embodiments the convolutional neural network 22 may contain a number of convolutional layers 24, a number of pooling layers 25 and a number of fully connected layers 26, just like other types of layers. Any given order of the layers may be chosen. Fully connected layers 26 may form the last layers before the output layer 27.

For example, the nodes 28 to 32 of one of the layers 23 to 27 within a convolutional neural network 22 may be understood as being arranged in a d-dimensional matrix or as a d-dimensional image. For example, in the two-dimensional case the value of a node 28 to 32 with the indices i, j in the nth layer 23 to 27 may be referred to as $x^{(n)}[i,j]$. The arrangement of the nodes 28 to 31 of a layer 23 to 27 does not have any effect on the calculations within the convolutional neural network 22 as such, since these effects are produced solely by the structure and the weights of the edges.

A convolutional layer 24 is for example characterized in that the structure and the weights of the ingoing edges form a convolution operation based on a specific number of kernels. For example, the structure and the weights of the ingoing edges may be chosen so that the values $$x_k^{(n)}$$

of the node 29 of the convolution layer 24 are determined as a convolution $$x_k^{(n)} = K_k * x^{(n-1)}$$

based on the values $x^{(n-1)}$ of the node 28 of the preceding layer 23. The convolution $*$ in the two-dimensional case may be defined as $$x_k^{(n)}[i,j] = (K_k * x^{(n-1)})[i,j] = \sum_{i'} \sum_{j'} K_k[i',j'] \cdot x^{(n-1)}[i-i',j=j'].$$

In this the kth kernel $K_k$ is a d-dimensional matrix, in this embodiment a two-dimensional matrix, that is usually small by comparison with the number of nodes 28 to 32, for example a 3×3 matrix or a 5×5 matrix. For example, this implies that the weights of the ingoing edges are not independent but are chosen so that that they create the above convolution equation. In the example for a kernel that forms a 3×3 matrix, only nine independent weights exist (wherein each entry of the kernel matrix corresponds to an independent weight), regardless of the number of nodes 28 to 32 in the corresponding layer 23 to 27. For example, for a convolution layer 24, the number of nodes 29 in the convolution layer 24 is equivalent to the number of nodes 28 in the preceding layer 23 multiplied by the number of convolution kernels.

When the nodes 28 of the preceding layer 23 are arranged as a d-dimensional matrix, the use of the plurality of kernels may be understood as adding a further dimension, that is also referred to as a depth dimension, so that the nodes 29 of the convolution layer 24 are arranged as a (d+1)-dimensional matrix. When the nodes 28 of the preceding layer 23 are already arranged as a (d+1)-dimensional matrix with a depth dimension, the use of a plurality of convolution kernels may be understood as an expansion along the depth dimension, so that the nodes 29 of the convolution layer 24 are equally arranged as a (d+1)-dimensional matrix, wherein the size of the (d+1)-dimensional matrix in the depth dimension is greater by the factor formed by the number of kernels than it is in the preceding layer 23.

The advantage of the use of convolution layers 24 is that the spatially local correlation of the input data may be exploited in that a local connection pattern between nodes of neighboring layers is created, for example by the fact that each node only has connections to a small range of the nodes of the preceding layer.

In the embodiment shown the input layer 23 includes thirty six nodes 28, that are arranged as a two-dimensional 6×6 matrix. The convolution layer 24 includes seventy two nodes 29, that are arranged as two two-dimensional 6×6 matrices, wherein each of the two matrices is the result of a convolution of the values of the input layer 23 with a convolution kernel. In the same way the nodes 29 of the convolution layer 24 may be understood as being arranged in a three-dimensional 6×6×2 matrix, wherein the last-mentioned dimension is the depth dimension.

A pooling layer 25 is characterized in that the structure and the weights of the ingoing edges as well as the activation function of their nodes 30 define a pooling operation based on a non-linear pooling function f. For example, in the two-dimensional case, the values $x^{(n)}$ of the nodes 30 of the pooling layer 25 may be calculated based on the values $x^{(n+1)}$ of the nodes 29 of the preceding layer 24 as $$x^{(n)}[i,j] = f(x^{(n-1)}[id_1, jd_2], \dots, x^{(n-1)}[id_1 + d_1 - 1, jd_2 + d_2 - 1]).$$

The number of nodes 29, 30 may be reduced by the value of a pooling layer 25, in that a number of $d_1 \times d_2$ neighboring nodes 29 in the preceding layer 24 is replaced by an individual node 30, that is calculated as a function of the values of the number of neighboring nodes 29. For example, the pooling function f may be a maximum function, an averaging or the L2 norm. For example, for a pooling layer 25 the weights of the ingoing edges may be defined and not modified by training.

The advantage of using a pooling layer 25 is that the number of nodes 29, 30 and the number of parameters is reduced. This leads to a reduction of the amount of calculation necessary within the convolutional neural network 22 and thus to a control of the overfitting.

In the embodiment shown the pooling layer 25 involves a max pooling layer, in which four neighboring nodes are replaced by just a single node, of which the value is formed by the maximum of the values of the four neighboring nodes. The max pooling is applied to each d-dimensional matrix of the previous layer; in this embodiment the max pooling is applied to each of the two two-dimensional matrices, so that the number of nodes is reduced from seventy two to eighteen.

A fully connected layer 26 is characterized in that a majority, for example all, edges between the nodes 30 of the previous layer 25 and the nodes 31 of the fully connected layer 26 are present, wherein the weight of each of the edges may be adapted individually. In this embodiment the nodes 30 of the preceding layer 25 and the fully connected layer 26 are shown both as two-dimensional matrices and also as non-contiguous nodes (shown as a row of nodes, the number of nodes has been reduced for better clarity). In this embodiment the number of nodes 31 in the fully connected layer 26 is equal to the number of nodes 30 in the preceding layer 25. In alternate forms of embodiments, the number of nodes 30, 31 may be different.

Above and beyond this, in this embodiment, the values of the nodes 32 of the output layer 27 are determined by the softmax function being applied to the values of the nodes 31 of the preceding layer 26. By application of the softmax function the sum of the values of all nodes 32 of the output layer 27 is one and all values of all nodes 32 of the output layer are real numbers between 0 and 1. When the convolutional neural network 22 is used for classification of input data, for example the values of the output layer 27 are interpreted as the probability of the input data falling into one of the different classes.

A convolutional neural network 22 may likewise have a ReLU layer, wherein ReLU is an acronym standing for "rectified linear units". For example, the number of nodes and the structure of the nodes within an ReLU layer is equivalent to the number of nodes and of structures of the nodes of the preceding layer. The value of each node in the ReLU layer may for example be calculated by applying a rectifier function to the value of the corresponding node of the preceding layer. Examples of rectifier functions are $f(x)=\max(0,x)$, the hyperbolic tangent or the sigmoid function.

Convolutional neural networks 22 may for example be trained based on the back propagation algorithm. In order to avoid an overfitting, regularization methods may be employed, for example dropout of individual nodes 28 to 32, stochastic pooling, use of artificial data, weight decay based on the L1 or the L2 norm or maximum norm restrictions.

Independent of the grammatical term usage, individuals with male, female or other gender identities are included within the term.

It is to be understood that the elements and features recited in the appended claims may be combined in different ways to produce new claims that likewise fall within the scope of the present embodiments. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present embodiments have been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for scattered radiation correction of projection images of an x-ray imaging, the method comprising:
   obtaining the projection images;
   optimizing, by a determination algorithm, a measure of quality by variation of correction parameters used within a framework of scattered radiation correction;
      wherein the determination algorithm is trained by machine learning using input data comprising a reconstructed three-dimensional image dataset or processing data that is chosen from the reconstructed three-dimensional image dataset and/or is determined depending on the reconstructed three-dimensional image dataset;
      wherein the reconstructed three-dimensional image dataset is based on corrected projection images;
      wherein a respective corrected projection image of the corrected projection images is a result of application of a correction algorithm to a respective one of the projection images;
      wherein the correction algorithm is parameterized by the correction parameters or by a subgroup of the correction parameters assigned to the respective projection image; and
   providing radiation scatter-corrected projection images by application of the correction algorithm to the respective projection image, wherein the correction algorithm is parameterized in accordance with the optimal correction parameters or by the subgroup of the optimal correction parameters assigned to the respective projection image obtained, and/or is a radiation scatter-corrected reconstructed three-dimensional image dataset, that is based on the radiation scatter-corrected projection images.

2. The computer-implemented method of claim 1, wherein the determination algorithm exclusively processes the processing data as input data, wherein the processing data comprises a number of two-dimensional slice images spaced apart from one another and/or oriented at an angle to one another or by precisely one two-dimensional slice image of the three-dimensional image dataset.

3. The computer-implemented method of claim 1, wherein the correction algorithm comprises the determination of an estimated scattered radiation distribution for the respective projection image, depending on the correction parameters or on the subgroup of correction parameters assigned to the respective projection image, wherein the corrected projection image is determined by subtraction of the estimated scattered radiation distribution from the projection image.

4. The computer-implemented method of claim 3, wherein the scattered radiation distribution is determined as a weighted sum of basic images, wherein the weighting factors with which the basic images are weighted in the weighted sum are predetermined by the correction parameters or by the subgroup of correction parameters assigned to the respective projection image.

5. The computer-implemented method of claim 4, wherein at least one of the basic images is predetermined depending on at least one of the correction parameters, wherein instances of the respective basic image resulting from a different choice of correction parameter may be converted into one another by an affine transformation or by a number of affine transformations applied one after another.

6. The computer-implemented method of claim 5, wherein the scattered radiation distribution or at least one of the respective basic images and/or at least one respective original image, on the basis of which a respective one of the basic images is determined, are predetermined by a two-dimensional Gaussian distribution and/or a two-dimensional B spline, wherein at least one parameter of the respective two-dimensional Gaussian distribution and/or of the respective two-dimensional B spline is predetermined by a respective one of the correction parameters.

7. A method for parameterization of a determination algorithm that is configured to determine a measure of quality, the method comprising:

predetermining a number of training datasets, that each comprise a number of pairs consisting of a reference projection image and a scattered radiation distribution assigned to the respective reference projection image;

generating a respective intermediate image by the assigned value of the assigned scattered radiation distribution being added in each case to the image values of the image points of the respective reference projection image;

determining a proportion of scattered radiation for the respective training dataset depending on the image values of the reference projection images of the training dataset and the value of the scattered radiation distribution assigned in each case; and minimizing a cost function that depends on the respective deviation between a measure of quality determined by the determination algorithm and the proportion of scattered radiation for the number of training datasets, by variation of a number of parameters of the determination algorithm;

wherein the determination algorithm processes as its input data a reconstructed three-dimensional image dataset or processing data that is chosen from the three-dimensional image dataset and/or is determined depending on the three-dimensional image dataset;

wherein the three-dimensional image dataset is based on intermediate images.

8. The method of claim 7, wherein for at least one of the training datasets, the reference projection images and a provisional scattered radiation distribution assigned to the respective reference projection image are determined by simulation of an imaging of a predetermined three-dimensional reference dataset, wherein the scattered radiation distribution contained in the training dataset assigned to the respective reference projection image is predetermined by a scaling and/or an affine transformation of the provisional scattered radiation distribution.

9. The method of claim 8, characterized in that a first scattered radiation distribution is predetermined as the weighted sum of a number of predetermined two-dimensional distribution functions with first weighting factors, wherein a second scattered radiation distribution is predetermined as the weighted sum of the predetermined two-dimensional distribution functions with second weighting factors that are different from the first weighting factors.

10. The method of claim 9, wherein a periodic function is used as at least one of the distribution functions.

11. The method of claim 10, wherein the period length of the periodic function is at least a fifth or at least a third of the image height and/or of the image width of the reference projection image assigned to the respective scattered radiation distribution.

12. The method of claim 7, wherein a first of the scattered radiation distributions is predetermined as a predetermined two-dimensional distribution function or as a weighted sum that comprises the predetermined two-dimensional distribution function as a summand, wherein a second of the scattered radiation distributions is predetermined as an affine transformation of the predetermined two-dimensional distribution function or as a weighted sum that comprises the affine transformation of the predetermined two-dimensional distribution function as a summand.

13. A non-transitory computer implemented storage medium that stores machine-readable instructions for scattered radiation correction, the machine-readable instructions comprising:

obtaining projection images;

optimizing, by a determination algorithm, a measure of quality by variation of correction parameters depending on the projection images, wherein the determination algorithm is trained by machine learning and processes as input data a reconstructed three-dimensional image dataset or processing data that is selected from the reconstructed three-dimensional image dataset and/or is determined depending on the reconstructed three-dimensional image dataset, wherein the reconstructed three-dimensional image dataset is based on corrected projection images, wherein a respective corrected projection image of the corrected projection images is a result of application of a correction algorithm to a respective one of the projection images, wherein the correction algorithm is parameterized by the correction parameters or by a subgroup of the correction parameters assigned to the respective projection image; and providing radiation scatter-corrected projection images by application of the correction algorithm to the respective projection image.

* * * * *